(12) United States Patent
Perez-Soler

(10) Patent No.: US 6,620,403 B2
(45) Date of Patent: Sep. 16, 2003

(54) IN VIVO CHEMOSENSITIVITY SCREEN FOR HUMAN TUMORS

(76) Inventor: Roman Perez-Soler, 564 1st Ave., Apt. 20T, New York, NY (US) 10016

( * ) Notice: Subject to any disclaimer, the term of this patent is extended or adjusted under 35 U.S.C. 154(b) by 0 days.

(21) Appl. No.: 09/841,669

(22) Filed: Apr. 24, 2001

(65) Prior Publication Data

US 2002/0031473 A1 Mar. 14, 2002

Related U.S. Application Data

(60) Provisional application No. 60/199,765, filed on Apr. 26, 2000.

(51) Int. Cl.$^7$ ................................................ A61K 49/00
(52) U.S. Cl. ........................ 424/9.2; 424/1.11; 424/9.1
(58) Field of Search ................................ 424/1.11, 9.1, 424/9.2

(56) References Cited

U.S. PATENT DOCUMENTS 6,160,166 A * 12/2000 Collins et al. ................ 562/16

* cited by examiner

*Primary Examiner*—Dameron L. Jones
(74) *Attorney, Agent, or Firm*—Watov & Kipnes, P.C

(57) ABSTRACT

A method of evaluating the chemosensitivity of a tumor to an anti-tumor agent in vivo is provided. The method comprises extracting a portion of a tumor from a human host and inserting the portion of the tumor into an immunodeficient mouse. The tumor portion is permitted to grow to a minimum preselected size to form a test tumor. An amount of an anti-tumor agent is administered to the immunodeficient mouse sufficient to determine whether the anti-tumor agent is effective in treating the test tumor. The anti-tumor activity of the anti-tumor agent on the test tumor is assessed.

18 Claims, 1 Drawing Sheet

IN VIVO CHEMOSENSITIVITY SCREEN FOR HUMAN TUMORS

The present application claims the benefit of priority from U.S. Provisional Application No. 60/199,765, filed Apr. 26, 2000.

FIELD OF THE INVENTION

The present invention relates generally to a non-human host model for human tumors. More particularly, this invention relates to a hon-human host model implanted with a human tumor obtained from a human host and utilized for assessing the chemosensitivity of the implanted human tumor to an anti-tumor agent.

BACKGROUND OF THE INVENTION

The lack of clinically relevant tumor models of different human cancers is a major obstacle in the development of new and effective treatments for cancer especially for treatment of individual patients. Although heterotransplants of certain human tumors have been successfully grown in non-human host subjects such as nude mice, such heterotransplants have never been appropriately been explored for prediction of in vivo chemosensitivity to anti-tumor agents.

Most potential anti-tumor agents discovered and tested in clinical trials are rarely approved for use in treatment of cancer. Typically, the majority of the potential anti-tumor agents tested are abandoned for lack of anti-tumor activity during Phase II clinical studies rather than intolerable and/or unpredictable toxicity. Some of the current in vitro anti-tumor agent screening systems utilized by the National Institute of Health and the pharmaceutical industry involve the use of human tumor cell lines derived from multiple sequential in vitro subcultures generated from human tumor explants. Such cell lines are well characterized from a molecular standpoint and are useful in identifying molecular determinants of in vitro sensitivity and/or confirming putative molecular mechanisms of action for the compounds of the anti-tumor agents being screened. Such screening systems have limited usefulness because most human tumors comprise accumulated genetic and molecular abnormalities which produces a high degree of phenotypic heterogeneity. Thus, the relevance of such screening systems for predicting in vivo clinical activity remains to be established.

New anti-tumor agents are routinely screened in vivo using human tumor xenografts which are grown subcutaneously in non-human host subjects such as nude mice. Typically, clinical trials of new anti-tumor agents measure tumor growth inhibition rather than tumor shrinkage as an indicator of anti-tumor activity. Such xenografts do not exhibit the heterogenous population of tumor cells which are representative of the human tumor from which they are derived. Furthermore, the vascularity and stroma of such xenografts are exclusively of murine origin. Generally, such xenografts have been selected to suit the putative molecular mechanism of the anti-tumor agent tested. This approach focuses on the proof of principle as to the in vivo model rather than accessing or screening the anti-tumor agent using a panel of clinically relevant and predictive models. If panels of in vivo experimental tumor models clinically representative of each major human cancer type were available, the selection criteria for pursuing the clinical development of novel anti-tumor agents would be stricter but the likelihood of identifying useful anti-tumor agents for particular tumors would be much higher. These would reduce the cost and patient resources required for anti-tumor agent development.

Similarly, if individualized models of human cancer were developed, such models would facilitate the process of selecting the optimal therapy for a particular patient's tumor. In vitro sensitivity tests using tumor cells derived from fresh tumor specimens have been known and used extensively. Such tests are typically more useful in confirming a tumor's resistance to anti-tumor agents which have been previously known to show little activity against a particular tumor rather than selecting the most active anti-tumor agent. In addition, in vitro assay systems can not account for the in vivo pharmacological determinants of anti-tumor activity.

SUMMARY OF THE INVENTION

The present invention is generally directed to a method of evaluating the chemosensitivity of a tumor to an anti-tumor agent in vivo. The method comprises generally of extracting a portion of a tumor from a human host and inserting it into a non-human host subject such as a nude immunodeficient mouse. The implanted tumor is permitted to grow to a minumum preseslected size to form a test tumor. Once the tumor reaches the prerequisite size, an amount of an anti-tumor agent is administered to the non-human host subject sufficient to determine whether the anti-tumor agent is effective in treating the test tumor. The test tumor is then examined to determine the anti-tumor activity of the anti-tumor agent. The present invention is also directed to a method of treating a patient suffering from the presence of a tumor is also contemplated.

In particular, one aspect of the present invention is directed to a method of evaluating the chemosensitivity of a tumor to an anti-tumor agent in vivo, comprising:
  a) extracting a portion of a tumor from a human host;
  b) inserting the portion of the tumor into a first non-human host subject;
  c) growing the tumor portion in the first non-human host subject to a minimum preselected size to form a test tumor;
  d) administering an amount of an anti-tumor agent into the first non-human host subject sufficient to determine whether the anti-tumor agent is effective in treating the test tumor; and
  e) assessing the anti-tumor activity of the anti-tumor agent on the test tumor.

Another aspect of the present invention is directed to a method of treating a patient suffering from the presence of a tumor, comprising:
  a) extracting at least one portion of the tumor from the patient;
  b) inserting the portion of the tumor into a first non-human host subject;
  c) growing the tumor portion in the first non-human host subject to a preselected minimum size to form a test tumor;
  d) administering an amount of an anti-tumor agent into the first non-human host subject sufficient to determine whether the anti-tumor agent is effective in treating the test tumor;
  e) assessing the anti-tumor activity of the anti-tumor agent; and, if positive
  f) administering an effective amount of the anti-tumor agent to said patient.

DETAILED DESCRIPTION OF THE INVENTION

Figure 1:
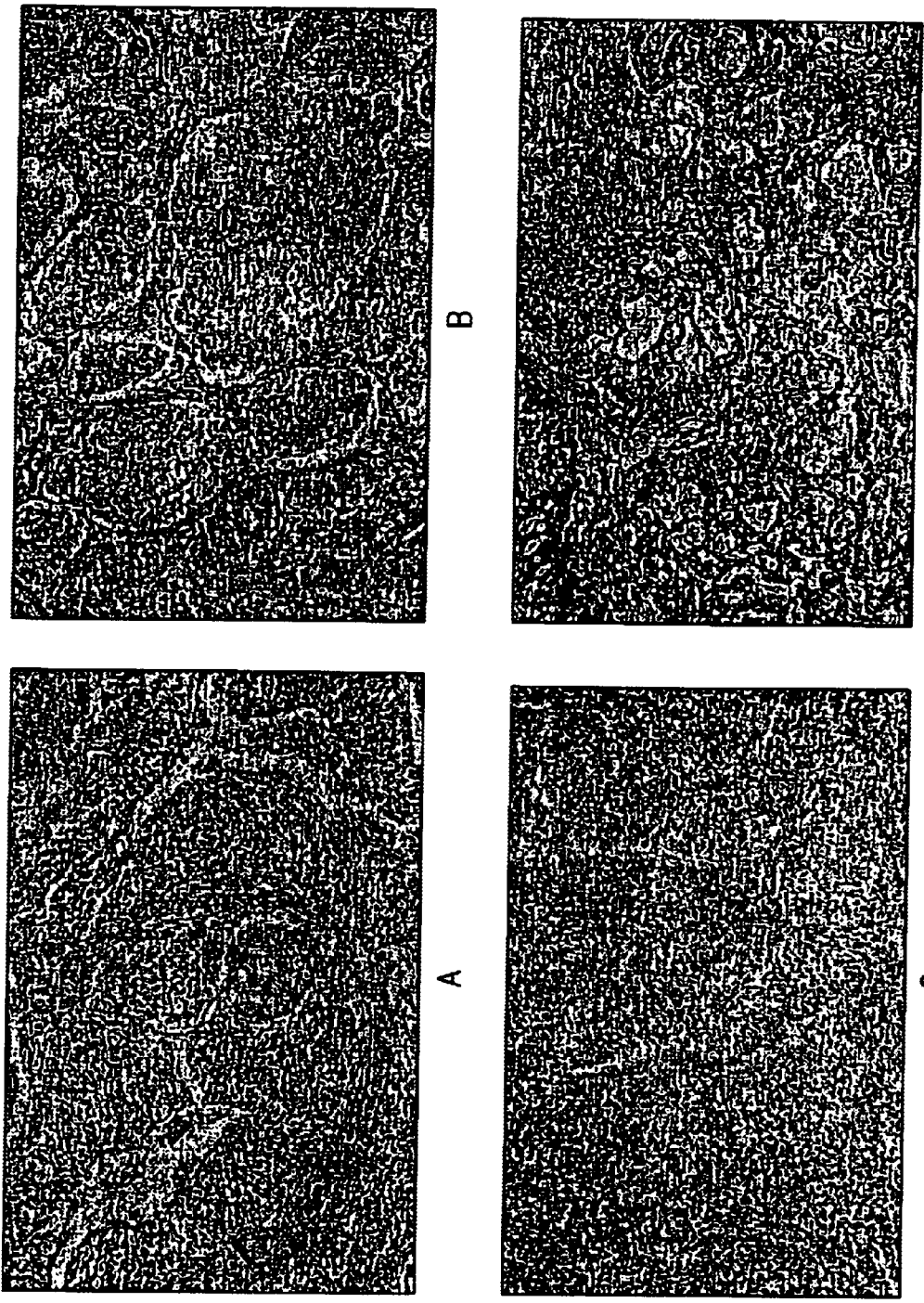
FIG. 1 shows a set of photomicrographs showing the morphological appearances of two of the transplanted tumors, squamous carcinoma (A), and adenocarcinoma (B) and their respective first successful implants in nude mice, (C) and (D).

The present invention is generally directed to a non-human host model implanted with a human tumor obtained from a human host utilized for assessing the chemosensitivity of the implanted human tumor to anti-tumor agents created in a manner that provides a system of screening anti-tumor agents for anti-tumor activity and of selecting the most optimal cancer treatment for a patient.

This invention deals with the use of heterotransplants of human tumors in nude mice both to screen and select new therapies for different tumors in general and to select the best therapy for the presence of tumor in individual patients. Many types of human tumors can be grown subcutaneously in immunodeficient mice. The morphological and kinetic characteristics of tumors change with each subsequent passage or generation of tumor implanted mice. Accordingly, it is important to use tumors from the early passages to test their response to different anti-tumor agents. The determinants of successful heterotransplantation are not known and generally, successful heterotransplantation is associated with poor clinical prognosis. The potential use of first and second heterotransplants of tumors as tumor models of potential clinical relevance to predict the anti-tumor activity of different anti-tumor agents and/or to select the most optimal treatment for an individual patient has not been explored before.

To prove this concept, a large panel of second passage human non-small cell lung cancer (NSCLC) heterotransplants had been developed and molecularly characterized for studying the sensitivity to paclitaxel, an anti-tumor agent. One hundred consecutive resected NSCLC tumors were heterotransplanted subcutaneously into nude mice. It will be understood that the present invention may comprise insertion or transplantation of tumors into the non-human host subject through other modes including, but not limited to, intravenous injection, intraperitoneal implantation, and implantation of the tumor directly into a solid organ.

The in vivo sensitivity to paclitaxel was studied in 34 successfully grown heterotransplants. The paclitaxel was intravenously administered to each mouse at a dosage rate of 60 mg/kg every 3 weeks. Treatment was initiated when the tumors reached a size of about 5 mm in diameter and strict standard clinical criteria (>50% tumor shrinkage) were used to define the tumor response. The heterotransplants were morphologically very similar to the original tumors. The response rate to paclitaxel was 21% (95% Cl 9–38%) which is equivalent to that reported in Phase II studies in patients with advanced NSCLC treated with paclitaxel alone. Tumor heterotransplants are thus proposed as relevant models to evaluate new potential anti-tumor agents for treatment of different cancers and to predict clinical response in individual patients. It is noted that the type of tumor utilized for evaluating chemosensitivity to anti-tumor agents comprises a range of cancers including, but not limited to, colon, head and neck, brain, melanoma, sarcoma, breast, ovarian, prostate, kidney and stomach cancers.

The results suggest that the heterotransplant models may be used to predict the response of human tumors to different agents and therefore help in the selection of the most optimal cancer therapy for individual patients. It will be understood that the chemosensitivity assay of the present invention may be used to screen a range of anti-tumor agents including, but not limited to, gemcitabine, taxotere, cisplatinum, carboplatinum, irinotecan, topotecan, adriamycin, and atoposide.

EXAMPLE 1

Patients and Tumors

Between December 1995 and February 1998, 100 fresh NSCLC tumor samples were obtained from the Pathology Department of th University of Texas M. D. Anderson Cancer Center. These samples were taken from 100 consecutive patients who underwent surgical resection for Stage I to IIIA primary NSCLC. None of these patients had undergone preoperative radiation therapy or preoperative chemotherapy. Referring to Table 1, the take rate is shown for 100 heterotransplanted tumors.

TABLE 1

Human NSCLC Heterotransplants Take Rate by Histology (n = 100)

| Histology | Number | Successful Growth/(%) | p-value |
|---|---|---|---|
| Adenocarcinoma | 44 | 13 (30%) | <0.05 |
| Squamous | 32 | 24 (75%) | <0.05 |
| Bronchioalveolar | 13 | 3 (23%) | <0.05 |
| Large Cell Undifferentiated | 9 | 5 (55%) | |
| Neuroendocrine | 1 | 1 (100%) | |
| Sarcomatoid | 1 | 0 (0%) | |
| Total: | 100 | 46 (46%) | |

The overall tumor take rate was 46% (95% Cl=36%–56%). The take rate was significantly higher (p<0.05) for squamous cell carcinomas (75%, 95% Cl 57%–89%) than for adenocarcinomas (30%, 95% Cl=17%–45%) and bronchioalveolar carcinomas (23%, 95% Cl=0%–54%). Large cell undifferentiated carcinoma had an intermediate take rate (5/9, 55%). Tumor take rate was independent of the implantation site of the tumor in the mouse. In 10 cases, the tumor initially appeared to have taken but spontaneously disappeared. These cases are considered temporary growths and thus not counted in the calculation of the successful take rate.

Tumor Implantation in Nude Mice

The fresh tumor samples were cut into 2–3 mm$^3$ pieces in sterile saline. Three or four pieces of non-necrotic tissue were injected subcutaneously into the lower back and anterior chest of 6 to 8 week old female Nu/Nu mice using a biomedical stainless steel implant needle and maintained under standardized conventional conditions. Animals transplanted with NSCLC tumors were checked for tumor growth over a 36 week period. Tumor formation measuring at least 5 mm in diameter was considered a positive take. Tumor formation was confirmed histologically in all cases. Temporary growth was defined as tumor formation followed by spontaneous regression before reaching a diameter of 5 mm. All other incidences were considered no growth.

The histological morphology of all successfully heterotransplanted tumors were compared with that of the resected tumors. There were no significant morphological differences between the tumors resected from the patients and the initial successful implants although the median mitotic index was slightly higher in the heterotransplants (9±6) than in the resected tumors (5±4). Referring to FIG. 1, a set of photographic representations are provided to show the morphology of two of the transplanted tumors with A representing squamous carcinoma and B representing adenocarcinoma and their successfully grown first implants, C and D, respectively.

The median time from the day of implantation from human to mouse to the day the tumor reached 1 cm in diameter was about 11 weeks (range 4–24 weeks) and the median weight doubling time which corresponds to a 20% increase in diameter was 18 days (range 11–40 days). These values are longer than those observed with commonly used NSCLC xenografts and much closer to those of human NSCLC which strongly suggests that the heterotransplanted tumors are accurate representatives of the original human tumors.

All successfully heterotransplanted tumors were subsequently transplanted several times. Changes in doubling time and mitotic index between the second and third passage were minimal in a group of 21 heterotransplants that were analyzed (doubling time 18±10 days for second passage tumors and 17±10 days for third passage tumors) (mitotic index was 10.9±6.6 for second passage tumors and 12.0±6.3 with p<0.05).

Paclitaxel Treatment and Assessment of Response

The therapeutic experiments were designed as a standard Phase II clinical study with a target response rate of 20%, the only difference being that the tumor response was assessed as the average of two animals rather than in a single subject as in the case of a human Phase II trial.

The tumor grown after implantation from human to mouse was resected and cut into pieces following the same procedure used for the original tumor sample as previously described above, and transplanted subcutaneously into several animals. Tumors from the first mouse to mouse passage were allowed to grow until reaching 5 mm in diameter, at which time the animals were split into two groups: 1) control group—no treatment; and 2) treated group. The treated group was administered 60 mg/kg paclitaxel intravenously as a bolus in the tail vein. Tumor measurements were performed twice a week and the tumor volume was calculated using the formula, $a \times b^2/2$ (a=longest diameter and b=shortest diameter). Partial tumor response was defined as an average reduction in the tumor volume of at least 50% in the animals of the treated group compared to the tumor volume measured in animals of the control group. Complete tumor response was defined as complete disappearance of the palpable tumor in both animals of the control group.

Referring to Table 2, the tumor response to paclitaxel is shown.

TABLE 2

Human NSCLC Heterotransplants Response to Paclitaxel

| Treatment | Number | Tumor Response/(%) Partial | Complete |
|---|---|---|---|
| First mouse to mouse passage | | | |
| Squamous carcinoma | 20 | 4 (20%) | 0 |
| Adenocarcinoma | 11 | 1 (9%) | 0 |
| Undifferentiated carcinoma | 2 | 1 | |
| Neuroendocrine carcinoma | 1 | 1 | |
| TOTAL | 34 | 7 (21%) | 0 (0%) |
| First mouse to mouse passage | | | |
| After first dose | 16 | 4 (24%) | 0 |
| After second dose | 16 | 1 (6%) | 3 (18%) |
| Second mouse to mouse passage | | | |
| First passage | 21 | 5 (24%) | 0 |
| Second passage | 21 | 6 (29%) | 0 |

Out of the total of 34 heterotransplants tested on the first mouse to mouse passage, 7 partial responses defined as a ≧50% reduction in tumor weight were observed after one single dose of paclitaxel for an overall response rate of 21% (95% Cl=9%–38%). There were no discrepancies in tumor response between the two animals in which the response was assessed. Since changes in tumor weight require smaller changes in tumor measurements, all partial responses were reevaluated using the standard clinical criteria of ≧50% in the product of the two largest diameters. All 7 partial responses were partial responses independently of the criteria used.

In 16 cases, the animals in the treatment group were again treated with a second dose of paclitaxel on the $21^{st}$ day to assess the effect of a second dose of therapy. A second dose of paclitaxel given on the $21^{st}$ day did not change the overall response rate observed with the single dose. However, the second dose resulted in the conversion of several partial responses into complete responses. In a total of 16 heterotransplants studied, there were 4/16 (25%, 95% Cl-7%–52%) partial responses after one dose. Three of these converted into complete response after two doses. None of the 12 heterotransplants that did not respond with one dose achieved a partial response after the second dose.

The therapeutic experiments were also performed in 21 cases using the second mouse to mouse transplants to assess whether sequential passaging alters the chemosensitivity to paclitaxel. In the 21 heterotransplants tested both on first and second mouse to mouse passages, the response rate were 24% (95% Cl: 8%–47%) and 29% (95% Cl: 11%–52%), respectively.

These results demonstrate that heterotransplants of NSCLC have an in vivo sensitivity to paclitaxel which is similar to that observed in clinical studies using paclitaxel alone in chemotherapy naive NSCLC patients. The reported overall response rate to a single agent paclitaxel in four Phase II studies that enrolled a total of 160 previously untreated patients with NSCLC is 24% (10, 21, 24, and 38%). The response rate in our series of 34 NSCLC heterotransplants was 21% (95% Cl: 9%–38%), which is essentially identical. These findings and the morphological similarity between the transplants and the original tumors strongly suggest their potential use to predict chemosensitivity.

The heterotransplantability of human NSCLC tumors in nude or SCID mice has been the subject of several studies. The take rate of 47% observed in our study is very similar to the take rate reported by these studies and is significantly higher than that reported for other common solid tumors. In particular, the take rate of hormone-dependent tumors such as breast and prostate cancer is typically about 10%. Except for histology, the tumor determinants of successful heterotransplantability remain undefined. Identification of determinants of transplantability is critical for increasing the take rate which would facilitate the general use of these models in predicting chemosensitivity in individual patients.

We have analyzed the relationship between tumor response and several baseline and post-therapy molecular markers that have been shown to play a role in paclitaxel sensitivity. The results are mostly confirmatory of previous studies of sensitivity to paclitaxel in different preclinical tumor systems and therefore constitute further evidence of the potential biological and clinical relevance of these tumors.

The possibility of using panels of human NSCLC heterotransplants to perform Phase II-like studies with new potential anti-tumor agents potentially effective against NSCLC has not been explored before. Ideally, tumors harvested from first mouse to mouse passages should be used which is possible since tumor fragments from a successful first take preserved frozen in 10% DMSO retain their ability to grow when re-implanted. Orthotopic implantation is possible and would allow determining tumor responses by non-invasive imaging techniques, thus providing more clinically relevant information on tumor sensitivity.

If the response rates using standard clinical criteria in Phase II-like studies conducted with the heterotransplants were similar to those observed in human Phase II studies with the same anti-tumor agents, as we have demonstrated with paclitaxel in this study, this observation would help validate the clinical relevance of these models and justify their use for selecting new potential anti-tumor agents for clinical development. Obviously, such relevance would still be limited to drugs whose metabolism in man and mouse are similar, and at doses that result in a similar AUC both in man at the maximum tolerated dose and the dose used in the mouse. This might exclude a few anti-tumor agents from being amenable to this type of screening.

The main thrust of this invention is to use these tumors as relevant models of individual patient tumors to predict sensitivity and therefore be useful tools for individualized selection of therapy. We are planning to demonstrate such use in asymptomatic patients with slow growing and in patients with early stage tumors who undergo resection and are treated with chemotherapy upon relapse, thus allowing a correlation between response upon relapse and sensitivity of the heterotransplant derived from the resected tumor.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A method of evaluating the chemosensitivity of a tumor to an anti-tumor agent in vivo, comprising:
    a) extracting a portion of a tumor from a human host;
    b) inserting the extracted portion of the tumor into a first non-human host;
    c) growing the extracted portion of the tumor in the first non-human host to a minimum preselected size to form a test tumor;
    d) extracting at least a portion of the test tumor from the first non-human host;
    e) inserting the extracted portion of the test tumor from the first non-human host into a second non-human host;
    f) administering an anti-tumor agent to the second non-human host in an amount sufficient to determine whether the anti-tumor agent is effective in treating the test tumor; and
    g) assessing the anti-tumor activity of the anti-tumor agent on the test tumor.

2. The method of claim 1 wherein the tumor is selected from the group consisting of colon cancer tumor, head and neck cancer tumor, brain cancer tumors, melanoma tumor, sarcoma tumor, breast cancer tumor, ovarian cancer tumor, prostate cancer tumor, kidney cancer tumor and stomach cancer tumor.

3. The method of claim 1 wherein the tumor is a human non-small cell lung cancer tumor.

4. The method of claim 1 wherein the first and second non-human hosts are the same species of animal.

5. The method of claim 1 wherein at least the first non-human host is an immunodeficient mouse.

6. The method of claim 1 comprising subcutaneously inserting the portion of the tumor into at least the first non-human host.

7. The method of claim 1 wherein the step of assessing the anti-tumor activity comprises measuring a reduction in size of the test tumor within the second non-human host.

8. The method of claim 1 wherein the anti-tumor agent is selected from the group consisting of paclitaxel, gemcitabine, taxotere, cisplatinum, carboplatinum, irinotecan, topotecan, adriamycin and atoposide.

9. A method of treating a patient suffering from the presence of a tumor, comprising:
    a) extracting at least one portion of the tumor from the patient;
    b) inserting the extracted portion of the tumor into a first non-human host;
    c) growing the extracted portion of the tumor in the first non-human host to a preselected minimum size to form a test tumor;
    d) extracting at least a portion of the test tumor from the first non-human host;
    e) inserting the extracted portion of the test tumor from the first non-human host into a second non-human host;
    f) administering an amount of an anti-tumor agent into the second non-human host sufficient to determine whether the anti-tumor agent is effective in treating the test tumor;
    g) assessing the anti-tumor activity of the anti-tumor agent; and, if positive
    h) administering an effective amount of the anti-tumor agent to said patient.

10. The method a claim 9 comprising repeating steps (a) through (g) until a positive acting anti-tumor agent is obtained.

11. The method of claim 9 wherein the tumor is selected from the group consisting of colon cancer tumor, head and neck cancer tumor, brain cancer tumor, melanoma tumor, sarcoma tumor, breast cancer tumor, ovarian cancer tumor, prostate cancer tumor, kidney cancer tumor and stomach cancer tumor.

12. The method of claim 9 wherein the tumor is a human non-small cell lung cancer tumor.

13. The method of claim 9 wherein the first and second non-human hosts are the same species of animal.

14. The method of claim 9 wherein at least the first non-human host is an immunodeficient mouse.

15. The method of claim 9 comprising subcutaneously inserting the portion of the tumor into at least first non-human host.

16. The method of claim 9 wherein the step of assessing the anti-tumor activity comprises measuring a reduction in size of the test tumor within the second non-human host.

17. The method of claim 9 comprising repeating steps (a) through (g) for a plurality of anti-tumor agents whereby if more than one positive anti-tumor agent is obtained, such positive anti-tumor agents are to be administered in combination with one another.

18. The method of claim 9 wherein the anti-tumor agent is selected from the group consisting of paclitaxel, gemcitabine, taxotere, cisplatinum, carboplatinum, irinotecan, topotecan, adriamycin and atoposide.

* * * * *